US007410983B2

(12) United States Patent
Watts et al.

(10) Patent No.: US 7,410,983 B2
(45) Date of Patent: Aug. 12, 2008

(54) COMBINATION OF FENOFIBRATE AND COENZYME Q10 FOR THE TREATMENT OF ENDOTHELIAL DYSFUNCTION

(75) Inventors: Gerald Francis Watts, Perth (AU); David Alan Playford, Perth (AU)

(73) Assignee: Fournier Laboratories Ireland Limited, Cork (IE)

( * ) Notice: Subject to any disclaimer, the term of this patent is extended or adjusted under 35 U.S.C. 154(b) by 0 days.

(21) Appl. No.: 10/399,639

(22) PCT Filed: Oct. 23, 2001

(86) PCT No.: PCT/EP01/12425

§ 371 (c)(1),
(2), (4) Date: Apr. 17, 2003

(87) PCT Pub. No.: WO02/34259

PCT Pub. Date: May 2, 2002

(65) Prior Publication Data

US 2004/0022778 A1    Feb. 5, 2004

(30) Foreign Application Priority Data

Oct. 26, 2000 (AU) .................. PR1038
Feb. 28, 2001 (AU) .................. PR3424

(51) Int. Cl.
*A61K 31/44* (2006.01)
*A61K 31/235* (2006.01)
*A61K 31/12* (2006.01)

(52) U.S. Cl. .................. 514/342; 514/543; 514/678
(58) Field of Classification Search .................. 514/342, 514/543, 678
See application file for complete search history.

(56) References Cited

U.S. PATENT DOCUMENTS

| 5,229,385 A | 7/1993 | Terao et al. |
| 5,880,148 A | 3/1999 | Edgar et al. |
| 6,028,109 A | 2/2000 | Willson |
| 6,423,742 B1 * | 7/2002 | Larson .................. 514/453 |

FOREIGN PATENT DOCUMENTS

| AU | 614577 | 8/1989 |
| EP | 0 419 905 | 4/1991 |
| EP | 1 034 791 | 9/2000 |
| WO | WO 97/28149 | 8/1999 |

OTHER PUBLICATIONS

Stedman's Medical Dictionary, 25th Edition, published 1990 by Williams & Wilkins (MD), P. 79, "angina".*
The Merck Manual of Diagnosis and Therapy, 14th Edition, published 1982 by Merck Sharpe & Dohme Research Laboratories, (NJ), pp. 494-511.*

Belichard et al. "Effect of a long-term treatment with lovastatin or fenofibrate on hepatic and cardiac ubiquinone levels in cardiomyopathic hamster". *Biochimica et Biophsical Acta*, vol. 1169, pp. 98-102 (1993).
Anderson TJ, Uehata A, Gerhard MD, et al. "Close relationship of endothelial function in the human coronary and peripheral Circulation". *J Am Coll Cardiol*, vol. 26, No. 1, pp. 235-241 (1995).
Cohen. "Dysfunction of vascular endothelium in diabetes mellitus". *Circulation*, vol. 97, Suppl V, pp. V67-V76 (1993).
Issemann et al. "Activation of a member of the steroid hormone receptor superfamily by peroxisome proliferators". *Nature*, vol. 347, pp.645-650 (1990).
Furchgott et al. "The obligatory role of endothelial cells in the relaxation of arterial smooth muscle by acetylcholine". *Nature*, vol. 299, pp. 373-376 (1980).
Garg et al. "Nitric oxide-generating vasodilators and 8-bromo-cyclic guanosine monophosphate inhibit mitogenesis and proliferation of cultured rat vascular smooth muscle cells". *J. Clin Invest*, vol. 83, pp. 1774-1777 (1989).
Keller et al. "Fatty acids and retinoids control lipid metabolism through activation of peroxisome proliferator-activated receptor-retinoid X receptor heterodimers". *Proc. Natl. Acad. Sci USA.*, vol. 90, pp. 2160-2164 (1993).
Moncada et al. "Nitric oxide: physiology, pathophysiology, and pharmacology". *Pharmacol.Rev*, vol. 43, No. 2, pp. 109-142 (1991).
Radomski et al. "Endogenous nitric oxide inhibits human platelet adhesion to vascular endothelium". *Lancet* vol. 2, pp. 1057:1058 (1987).
Rubanyi. "The role of endothelium in cardiovascular homeostasis and diseases". *J Cardiol Pharmacol* vol. 22, Ssuppl 4, pp. 51-514 (1993).
Sax et al. "Impaired forearm vasodilator reseve in patients with microvascular angina. Evidence of a generalized disorder of vascular function?". *New England Journal of Medicine*, vol. 317, pp. 1366-1370 (1987).
Schachinger et al. "Prognostic impact of coronary vasodilator dysfunction on adverse long-term outcome of coronary heart disease". *Circulation*, vol. 101, pp. 1899-1906 (2000).
Suwaidi et al. "Long term follow-up of patients with mild coronary artery disease and endothelial dysfunction". *Circulation*, vol. 101, pp. 948-954 (2000).

(Continued)

*Primary Examiner*—Raymond J Henley, III
(74) *Attorney, Agent, or Firm*—Merchant & Gould P.C.

(57) ABSTRACT

The present invention relates to a combination of a peroxisome proliferator activated receptor (PPAR) activator and a benzoquinone and their use in treating and/or preventing disorders characterized by endothelial dysfunction, such as cardiovascular disease, strokes and myocardial infarction. According to a preferred embodiment of the invention the benzoquinone or precursor thereof is a ubiquinone or precursor thereof, more preferably, coenzyme $Q_{10}$ or a precursor thereof, and the PPAR activator is a fibrate or a thiazolidinedione, more preferably fenofibrate.

2 Claims, 2 Drawing Sheets

OTHER PUBLICATIONS

Watts et al. "Dyslipoproteinemia and hyperoxidative stress in the pathogenesis of endothelial dysfunction in non-insulin dependent diabetes mellitus: an hypothesis". *Atherosclerosis*, vol. 141, pp. 17-30 (1998).

Widlansky et al., "The Clinical Implications of ENdothelial Dysfunctionn,", *J. Am. Coll. Cardiol.*, 2003; 42:1149-60.

Modena et al., "Prognostic Role of Reversible Endothelial Dysfunction in Hypertensive Postmenopausal Women," *J. Am. Coll. Cardiol.*, 2002; 40:505-10.

\* cited by examiner

COMBINATION OF FENOFIBRATE AND COENZYME Q10 FOR THE TREATMENT OF ENDOTHELIAL DYSFUNCTION

This application is a 371 of PCT/EP01/12425 filed Oct. 23, 2001.

FIELD OF THE INVENTION

The present invention relates to a combination of a peroxisome proliferator activated receptor (PPAR) activator and a benzoquinone and their use in treating and/or preventing disorders characterized by endothelial dysfunction, such as cardiovascular disease, strokes and myocardial infarction.

BACKGROUND TO THE INVENTION

The burden of cardiovascular disease is increasing in both developed and developing countries. This relates to an acceleration in the incidence of diabetes and obesity as well as to other cardiovascular risk factors, including hypercholesterolaemia, hypertension and smoking. All these conditions have in common a mechanism of vascular abnormality termed endothelial dysfunction (Rubanyi, 1993).

Nitric oxide (NO), a chemically unstable radical formed by enzymatic conversion of L-arginine in the presence of molecular oxygen, elicits relaxation of vascular smooth muscle cells. NO also counteracts platelet adhesion and aggregation. NO is released from endothelial cells by the action of acetylcholine (ACh). Failure of the vascular endothelium to elicit NO-mediated vasodilatation may be due to decreased formation of NO, increased degradation of NO and/or decreased biological sensitivity to NO. Irrespective of the mechanism this is referred to as endothelial dysfunction.

The vascular endothelium is also the site of formation of other vasodilator agents (e.g. prostacyclin, endothelium-derived hyperpolarizing factor), as well as vasoconstrictive factors (e.g. thromboxane A2, endothelin).

Endothelium dysfunction is highly relevant to vascular disease and occurs chiefly as a consequence of disturbances in the L-arginine/NO pathway.

Its occurrence in type 2 diabetes, for example, is extensively supported by both in vitro and in vivo studies (Cohen, 1993; Watts, 1998). Indeed, endothelial dysfunction may be the initiating event in the process of atherosclerosis eventually resulting in clinical coronary artery disease. In hypercholesterolemic subjects, impaired endothelium-dependent vasodilatation is evidenced before the development of atherosclerosis. In patients with type 2 diabetes endothelial function is abnormal even in the absence of elevated plasma LDL cholesterol concentration.

Endothelial dysfunction in diabetes may have implications not only for coronary artery disease, but also for peripheral vascular disease and retinopathy. Experimental and clinical studies support the concept that dyslipidemia (in particular increased circulatory concentrations of modified, small dense LDL), as well as hyperoxidative stress, are closely related to the development of endothelial dysfunction as a consequence of changes in the disposal of nitric oxide NO.

Oxidative stress represents a challenge to normal bodily functions. It may arise from an increase in exposure to free radicals/oxidants or may be a result of a decrease in antioxidant capacity. Oxidative stress is caused by reactive oxygen species which can be of both endogenous or exogenous origin. Endogenous sources of free radicals, such as the superoxide anion $O_2^-$, include endothelial cells, activated neutrophils and mitochondria. The term reactive oxygen species includes not only oxygen-centred radicals (e.g. superoxide and hydroxyl), but also non-radical derivatives of oxygen ($H_2O_2$), singulet oxygen and HOCl. In diabetes, as well as in myocardial infarction, stroke and inflammation, there is an increase in plasma levels of lipid hydroperoxides which are formed through a free radical-mediated mechanism from polyunsaturated fatty acids.

Accordingly, given the association between oxidative stress, endothelial dysfunction and a range of important disorders there is a need to provide an effective treatment for endothelial dysfunction caused by oxidative stress. In particular, type 2 diabetes is associated with a markedly increased risk of cardiovascular disease, its major complication.

Treatments have not been shown to be effective. There is a major need for new preventative and therapeutic strategies for cardiovascular disease.

DISCLOSURE OF THE INVENTION

Accordingly, the present invention provides a composition comprising a peroxisome proliferator activated receptor (PPAR) activator and a benzoquinone of formula I:

Formula I in which:
R1, R2 and R3 independently are:
an alkyl group having 1 to 8 carbon atoms, or
an alcoxy group having 1 to 8 carbon atoms;
R4 is:
an hydrogen atom,
an hydrocarbyl group having 1 to 60 carbon atoms,
a OR5 radical,
an SR6 radical,
a N(R7)(R8) radical,
a nitro group, or
a carboxyl group;
R5, R6, R7 and R8 being independently:
a hydrogen atom, or
an alkyl group having 1 to 20 carbon atoms;

or a precursor thereof capable of being metabolized in the human or animal body to said benzoquinone;

or a pharmaceutically acceptable salt thereof.

In one preferred embodiment of the invention, said benzoquinone is of the formula (I) in which $R_4$ is an alkenyl group or a polyalkenyl group, preferably a group of formula:

in which n is an integer of from 1 to 12, preferably from 6 to 11.

Preferably the benzoquinone or precursor thereof is a ubiquinone or precursor thereof, more preferably, coenzyme $Q_{10}$ or a precursor thereof.

Preferably, the PPAR activator is a PPARα or a PPARγ activator.

Preferably, the PPAR activator is a fibrate or a thiazolidinedione, more preferably fenofibrate.

The PPAR activator, such as fenofibrate, may be co-micronised with a solid surfactant. Preferably, the solid surfactant is sodium lauryl sulphate.

The present invention also provides a pharmaceutical composition comprising a composition of the invention together with a pharmaceutically acceptable carrier or diluent.

The present invention further provides a method of treating or preventing a disorder characterized by endothelial dysfunction in an individual which method comprises administering to said individual an effective amount of a peroxisome proliferator activated receptor (PPAR) activator and a benzoquinone of formula I or a precursor thereof capable of being metabolized in the human or animal body.

Typically, the disorder is selected from cardiovascular disease, hypertension, stroke, myocardial infarction, peripheral vascular disease, angina pectoris, cardiac failure, diastolic and/or systolic ventricular dysfunction, macro and microangiopathy in patients with diabetes, and tissue damage related to ischemia or reperfusion.

The PPAR activator and benzoquinone may, for example, be administered separately, sequentially or concomitantly.

The present invention also provides a peroxisome proliferator activated receptor (PPAR) activator and a benzoquinone of formula I, or a precursor thereof capable of being metabolized in the human or animal body to said benzoquinone, for use in therapy.

Further, the present invention provides the use of a peroxisome proliferator activated receptor (PPAR) activator and a benzoquinone of formula I, or a precursor thereof capable of being metabolized in the human or animal body to said benzoquinone, in the manufacture of a medicament for use in treating a disorder characterized by endothelial dysfunction, as defined above.

Further still, the present invention provides a method for producing a composition of the invention which method comprises admixing said PPAR activator and benzoquinone.

The present invention also provides a method for producing a pharmaceutical composition of the invention which method comprises admixing said PPAR activator and benzoquinone with a pharmaceutically acceptable carrier or diluent.

BEST MODE(S) FOR CARRYING OUT THE INVENTION

Throughout the specification, unless the context requires otherwise, the word "comprise" or variations such as "comprises" or "comprising", will be understood to imply the inclusion of a stated integer or group of integers but not the exclusion of any other integer or group of integers.

PPAR Activators

The peroxisome proliferator activated receptor (PPAR) (Issemann, 1990) is a member of the family of ligand-activated nuclear receptors including the estrogen receptor, the retinoic acid receptor (RXR) and the androgen receptor. These nuclear receptors are activated by the binding of a ligand, for example, estrogen, in the case of the estrogen receptor. The activation of the receptor enables the latter to then bind to a specific DNA sequence, termed the responsive element, in the promoter of a given gene leading thus to either an increase or in some cases a decrease in the transcription of the target gene.

PPAR is present as 2 main subtypes, PPARα and PPARγ. Both subtypes do not bind alone to the DNA promoter but must first dimerize with RXR. This heterodimer, composed of either PPARα and RXR or PPARγ and RXR then binds to a specific DNA sequence in the promoter, the peroxisome proliferator responsive element. The endogenous ligands for PPARα and PPARγ are not known but are thought to be long chain fatty acids and/or their metabolites (Keller, 1993). PPARα and PPARγ control the expression of genes involved in fatty acid and energy utilisation.

PPAR activators according to the present invention are activators of PPARα and PPARγ. A number of PPAR activators are known in the art including the fibrate and thiazolidinedione classes of drugs, for which fenofibrate and rosiglitazone, respectively, are well known examples. Activators of PPARα and PPARγ have overlapping as well as distinct pharmacological effects. In humans as well as in animal models, activation of PPARα with a fibrate, such as fenofibrate, or PPARγ with rosiglitazone leads to comparable lowering of serum triglycerides. Both PPARα and PPARγ are expressed in muscle, while PPARα is preferentially expressed in hepatocytes and PPARγ in adipocytes. Fibrates mainly activate PPARα but bezafibrate has been shown to activate both PPARα and PPARγ. Similarly, rosiglitazone, an activator of PPARγ can also modify the expression of genes normally controlled by PPARα.

Preferred PPAR activators according to the present invention are agonists of PPARα activity. It is particularly preferred to use fibrates, such as fenofibrate. A further example of a member of the fibrate family is given in U.S. Pat. No. 6,028,109.

Benzoquinones

Benzoquinones for use in the present invention are a benzoquinone of formula I:

Formula I in which:
R1, R2 and R3 independently are
an alkyl group having 1 to 8 carbon atoms, or
an alcoxy group having 1 to 8 carbon atoms;
R4 is:
an hydrogen atom,
an hydrocarbyl group having 1 to 60 carbon atoms,
a OR5 radical, an SR6 radical,
a N(R7)(R8) radical,
a nitro group, or
a carboxyl group; or
R5, R6, R7 and R8 being independently:
a hydrogen atom,
an alkyl group having 1 to 20 carbon atoms;

or a precursor thereof capable of being metabolized in the human or animal body to said benzoquinone;

or a pharmaceutically acceptable salt thereof.

In the description and the claims, the term "hydrocarbyl" is understood as meaning an organic group comprising at least C and H. If the hydrocarbyl group comprises more than one C, then those carbon atoms may be linked to each other directly by a single, double or triple bond, or indirectly by the intermediary of a suitable element or hetero atoms such as for example oxygen, sulfur or nitrogen atoms or a suitable group such as a carbonyl group.

The hydrocarbyl group may optionally comprise one or more suitable substituants. Examples of such substituants may include a halogen atom, an alkyl group having 1 to 8 carbon atoms, an alcoxy group having 1 to 8 carbon atoms, a nitro group, a bis alkyl group having 1 to 16 carbon atoms, a cyclic group having 1 to 16 carbon atoms, etc.

The hydrocarbyl group may be any one of an alkyl group, an alcoxy group, a polyalcoxy group, an aryl group, an acyl group, an alkenyl group, a polyalkenyl group, including combinations thereof (e.g. an arylalkyl group), which group may optionally contain one or more hetero atoms or one or more substituants on the chain or rings, as defined above.

The hydrocarbyl group is preferably a hydrocarbon group. Here the term "hydrocarbon" means any one of an alkyl group, an alkenyl group, an alkynyl group, which groups may be linear, branched or cyclic, or an aryl group, or combinations thereof (e.g. an arylalkyl group). The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

In one preferred embodiment of the invention R1, R2 and R3 are each independently a lower alkyl group or a lower alkoxy group. The term "lower alkyl group" means a straight-chain or branched alkyl group having 1 to 8 carbon atoms, and examples thereof include methyl, ethyl, propyl, isopropyl, butyl, isobutyl, sec-butyl, tert-butyl, pentyl (amyl), isopentyl, neopentyl, tert-pentyl, 1-methylbutyl, 2-methylbutyl, 3-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and octyl groups. Among them, methyl, ethyl, propyl, isopropyl groups, etc., are preferable.

The term "lower alkoxy group" means a lower alkoxy group derived from the above-described lower alkyl group, such as methoxy, ethoxy and n-propoxy groups. Among them, a methoxy group is most preferred.

Preferably, R4 is an alkenyl group or a polyalkenyl group, i.e. a group having one or more double bonds in any portion of an alkyl group. R4 may comprise from 1 to 12, such as 6 to 11, preferably 9 or 10 repeats of an isoprenoid unit, such as 3-methyl-2-butene-1,4 diyl unit.

Preferably, R5, R6, R7 and R8 may each independently be H or $C_1$ to C4 alkyl.

Compounds of the present invention may contain one or more asymmetric carbon atoms and/or one or more non-aromatic carbon-carbon double bonds and may therefore exist in two or more stereoisomeric forms. Thus, the present invention also provides individual stereoisomers of the compounds of the formula (I), as well as mixtures thereof, including compositions comprising the same.

Separation or diastereoisomers or cis and trans isomers may be achieved by conventional techniques, e.g. by fractional crystallisation, chromatography or HPLC of a stereoisomeric mixture of a compound of the formula (I) or a suitable salt or derivative thereof. An individual enantiomer of a compound of the formula (I) may also be prepared from a corresponding optically pure intermediate or by resolution, such as by HPLC of a racemate using a suitable chiral support or by fractional crystallisation of the diastereoisomeric salts formed by reaction of a racemate with a suitable optically active acid or base.

Benzoquinones for use in the therapeutic methods of the present invention should have antioxidant properties, such as the ability to scavenge active oxygen species. In addition, benzoquinones for use in the therapeutic methods of the present invention will clearly need to be physiologically acceptable upon administration and not cause excessive side effects. For example, they should not be unduly toxic to patients. The toxicity of benzoquinones may be determined using a variety of methods known in the art including in vitro whole cell assays and $LD_{50}$ animal tests.

U.S. Pat. No. 5,229,385, for example, describes a range of benzoquinone derivatives having antioxidant properties which may be used therapeutically. EP-A-419905 also describes a number of benzoquinone derivatives suitable for therapeutic use.

It will be appreciated by the skilled person that since the benzoquinone coenzyme $Q_{10}$ is synthesised in vivo from precursor molecules, it may be possible to administer a benzoquinone according to the present invention by means of a precursor that is capable of being converted to a benzoquinone by the same biosynthetic pathways that produce coenzyme $Q_{10}$. Typically, a precursor will be an immediate precursor, that is to say a molecule structurally related to the benzoquinone and that needs to undergo only a small number of steps in the biosynthetic pathway before it is converted to a benzoquinone of formula I. It is generally preferred to administer precursors that are processed by parts of the coenzyme $Q_{10}$ biosynthetic pathway which are unique to coenzyme Q. For example, chorismate is converted in the body to p-aminobutyric acid, p-hydroxybenzoic acid, prephenate (which leads to phenylalanine and tyrosine) and is therefore not an immediate precursor since it supplies several pathways. By contrast, p-hydroxybenzoic acid is used only in the synthesis of ubiquinones and may be considered to be an immediate precursor.

The skilled person will appreciate that the reason for preferring immediate precursors is to avoid effects on other biosythetic pathways which may have a deleterious effect on the patient.

The skilled person will also appreciate that the benzoquinones according to the present invention are reduced in the human or animal body to a benzoquinol. Consequently, since it may be possible to administer benzoquinones in their reduced or oxidised state, references to benzoquinones throughout mean both the quinone and reduced quinol forms.

It is particularly preferred to use coenzyme Q, a naturally occurring agent which acts as an electron carrier in the mitochondrial electron transfer in the respiratory chain and which possesses several other functions. CoQ is synthesised from condensation of a benzoquinone ring and a hydrophobic side chain varying in size between species with elongation through a trans-prenyl transferase with multiple repeats of isopentenyl diphosphate units. In humans the side chain is composed of ten such repeats, that is the origin of its designation as $CoQ_{10}$.

In vivo the oxidized $CoQ_{10}$ is converted to reduced $CoQ_{10}H_2$ or ubiquinol-10, a potent antioxidant in plasma, in lipoproteins and in tissues. It scavenges in plasma free radicals produced by lipid peroxidation. $CoQ_{10}$ treatment has been previously demonstrated to be safe at doses up to 300 mg daily for the patient and in many countries different presentations are available over the counter. From previous evidence and as confirmed herein, $CoQ_{10}$ plasma levels increase 3 to 4 fold after administration of 200 mg daily.

Administration

The amount of PPAR activator and benzoquinone or precursor thereof which is required to achieve the desired biological effect will, of course, depend on a number of factors, for example, the mode of administration and the precise clinical condition of the recipient. The following routes of administration and dosages described are intended only as a guide since a skilled practitioner will be able to determine readily the optimum route of administration and dosage for any particular patient and condition.

In general, the daily dose of each component will be in the range of 0.1 mg-100 mg/kg, typically 0.1-20 mg/kg. An intravenous dose may, for example, be in the range of 0.01 mg to 0.1 g/kg, typically 0.01 mg to 10 mg/kg, which may conveniently be administered as an infusion of from 0.1 µg to 1 mg, per minute. Infusion fluids suitable for this purpose may contain, for example, from 0.01 µg to 0.1 mg, per milliliter. Unit doses may contain, for example, from 0.1 µg to 1 g of each component. Thus ampoules for injection may contain, for example, from 0.1 µg to 0.1 g and orally administrable unit dose formulations, such as tablets or capsules, may contain, for example, from 0.1 mg to 1 g.

Preferably, the PPAR activator, particularly fenofibrate, is administered in an amount from about 50 to 450 mg daily and the benzoquinone or precursor thereof is administered in an amount from about 10 to 400 mg daily.

The PPAR activator and benzoquinone or precursor thereof may be administered as the compounds per se, but are preferably presented with an acceptable carrier or diluent in the form of a pharmaceutical composition. The carrier or diluent may be a solid or a liquid, or both, and is preferably formulated with the activator and benzoquinone as a unit-dose formulation, for example, a tablet, which may contain from 0.05% to 95% by weight of the active component.

The formulations include those suitable for oral, rectal, topical, buccal (e.g. sublingual) and parenteral (e.g. subcutaneous, intramuscular, intradermal or intravenous) administration.

Formulations suitable for oral administration may be presented in discrete units, such as capsules, cachets, lozenges or tablets, each containing a predetermined amount of a PPAR activator and/or benzoquinone; as a powder or granules; as a solution or a suspension in an aqueous or non-aqueous liquid; or as an oil-in-water or water-in-oil emulsion.

In general, the formulations are prepared by uniformly and intimately admixing the active PPAR activator and/or benzoquinone with a liquid or finely divided solid carrier, or both, and then, if necessary, shaping the product. For example, a tablet may be prepared by compressing or moulding a powder or granules of the PPAR activator and/or benzoquinone optionally with one or more accessory ingredients. Compressed tablets may be prepared by compressing, in a suitable machine, the compound in a free-flowing form, such as a powder or granules optionally mixed with a binder, lubricant, inert diluent and/or surface active/dispersing agent(s). Moulded tablets may be made by moulding, in a suitable machine, the powdered compound moistened with an inert liquid diluent.

Formulations suitable for buccal (sub-lingual) administration include lozenges comprising a PPAR activator and/or benzoquinone in a flavoured base, usually sucrose and acacia or tragacanth, and pastilles comprising the activator in an inert base such as gelatin and glycerin or sucrose and acacia.

Formulations of the present invention suitable for parenteral administration conveniently comprise sterile aqueous preparations of a PPAR activator and/or benzoquinone, preferably isotonic with the blood of the intended recipient. These preparations are preferably administered intravenously, although administration may also be effected by means of subcutaneous, intramuscular, or intradermal injection. Such preparations may conveniently be prepared by admixing the activator with water and rendering the resulting solution sterile and isotonic with the blood. Injectable compositions according to the invention will generally contain from 0.1 to 5% w/w of the activator and 0.1 to 5% w/w of the benzoquinone.

Formulations suitable for rectal administration are preferably presented as unit-dose suppositories. These may be prepared by admixing a PPAR activator and/or benzoquinone with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanolin, polyethylene glycols, alcohols, and combinations of two or more thereof. The PPAR activator and/or benzoquinone are generally present at a concentration of from 0.1 to 15% w/w of the composition, for example, from 0.5 to 2%.

Preferably, the PPAR activator, such as fenofibrate is co-micronised with a solid surfactant (for example as described in AU-A-614577). A particularly preferred solid surfactant is sodium lauryl sulphate. Typically, the solid surfactant is used in an amount of from 1 to 4%.

The PPAR activator and benzoquinone may be administered separately, sequentially or simultaneously (such as when administered as a composition comprising both the PPAR activator and a benzoquinone).

In addition, it may also be desirable to administer, in addition to the PPAR activator and/or benzoquinone according to the present invention, further components, such as pharmaceutically active compounds that improve vascular condition. As specific examples, it may be desirable to administer aspirin, an antiotensin converting enzyme inhibitor and/oror a calcium channel blocker to the patients before or during treatment with the PPAR activator and benzoquinone.

Therapeutic Uses

The mechanism of the improvement of vascular function with the combination of a PPAR activator such as fenofibrate and a benzoquinone such as $CoQ_{10}$ is likely to be due to a direct effect on the vascular wall, independent to a large extent from the lipid lowering effects of the PPAR activator. This synergy could be explained at least in part by either an interaction with the formation, diffusion or action of endogenous NO or endothelium-derived hyperpolarizing factor remains possible. This is supported by the findings with acetylcholine (Ach), sodium nitroprusside (SNP) and the co-infusion of ACh+$N^G$-monomethyl-L-arginine (L-NMMA) in the setting of aspirin therapy. Pretreatment with aspirin also simulates best clinical practice of preventive medicine, given that aspirin has been shown to diminish cardiovascular events in patients with and without diabetes.

The improvement of endothelial dysfunction provided by the combination of a PPAR activator such as fenofibrate and a benzoquinone such as $CoQ_{10}$ constitutes a new therapeutic approach which is easy to implement.

Beyond the synergy demonstrated herein with a combination of fenofibrate and coenzyme $Q_{10}$, similar effects could be obtained with a combination of other benzoquinone antioxidants (or their precursors) and other fibrates or PPAR activators which share with fenofibrate an effect on the expression of multiple genes involved in atherosclerosis, lipid metabolism and regulation of vascular wall function.

Thus, a combination of a PPAR activator and a benzoquinone may be used to treat or prevent disorders characterised by endothelial dysfunction, or an increased risk of endothelial dysfunctions. Examples of such disorders include cardiovascular events, cardiovascular disease, hypertension, stroke, myocardial infarction, peripheral vascular disease, angina pectoris, cardiac failure, diastolic and/or systolic ventricular dysfunction, macro and microangiopathy in patients with diabetes, and tissue damage related to ischemia and reperfusion. In particular, a combination of a PPAR activator and a benzoquinone may be used to treat patients with type 2 diabetes.

More specifically, the physiological effects associated with the administration of a combination of a PPAR activator and a benzoquinone may result in one or more of the following: improved vessel tone, reduced blood clotting, reduced platelet aggregation, reduced blood pressure and increased blood flow to the heart, reduced smooth muscle cell proliferation and inhibition of leucocyte chemotaxis.

Accordingly the present invention also provides a method of improving vessel tone, reducing blood clotting, reducing platelet aggregation, reducing blood pressure and increasing blood flow to the heart, reducing smooth muscle cell proliferation, and/or inhibiting leucocyte chemotaxis in a patient which method comprises administering to said patient an effective amount of a PPAR activator and a benzoquinone.

Vessel tone, platelet aggregation, blood pressure and blood flow, smooth cell proliferation and leucocyte chemotaxis may be measured using standard techniques prior to and during treatment to determine whether the PPAR activator and a benzoquinone are achieving the desired effect (see for example Furchgott, 1980; Garg, 1989; Radomski, 1987 and Moncada, 1991).

The present invention will now be described further by way of examples which are intended to be illustrative only and non-limiting.

EXAMPLES

Introduction

We have tested a combination of a peroxisome proliferator activated receptor (PPAR) activator, namely fenofibrate, and coenzyme $Q_{10}$ for the treatment of vascular dysfunction in a randomized clinical trial involving patients with type 2 diabetes.

The results obtained demonstrate for the first time a synergism between a lipid lowering agent (the PPAR activator) and a radical scavenger in reducing vascular dysfunction. This synergistic effect was considered to be both statistically significant and clinically relevant. Support for the clinical relevance of these finding is also provided by studies showing an association between endothelium dysfunction in peripheral arteries and endothelium dysfunction in the coronary arteries (Anderson, 1995; Sax, 1987) as well as longitudinal data showing that endothelial dysfunction predicts future coronary events (Suwaidi, 2000; Schachinger, 2000). Compared with treatment with fenofibrate alone, the combination of fenofibrate with Coenzyme Q improves endothelial dysfunction and potentially reduces the progression of macro- and microvascular disease in type 2 diabetes. We would anticipate this to result in improvements with respect to coronary heart disease, peripheral vascular disease, ischemic stroke, renal disease and retinopathy in diabetes patients and by extension, to subjects with insulin resistance, hypertension and obesity.

Study Design and Methods:

Eighty dyslipidaemic patients with well controlled type 2 diabetes were randomised double-blind in a 2×2 factorial study to receive fenofibrate (F), $CoQ_{10}$ (Q), fenofibrate and $CoQ_{10}$ (FQ), or placebo (P) for 12 weeks. Male or female patients aged less than 70 years and without severe obesity (Body Mass Index below 35 kg/m$^2$) were included after a 6 week run-in period if they had Haemoglobin A1c below 9%, total cholesterol below 6.5 mmol/l and either triglyceride above 1.8 mmol/l or HDL cholesterol below 1 mmol/l. The two therapeutic agents alone or in combination were given each as 200 mg once daily. Capsules identical in appearance to each agent but containing placebo were given to maintain the double-blind nature of the study.

Evaluations of vascular function were carried out by bilateral venous occlusion plethysmography at weeks 0 and 12. These consisted of serial measurements of forearm blood flow before and after intra-brachial artery infusion of acetylcholine (ACh 7.5, 15 and 30 μg/min), sodium nitroprusside (SNP 1.5, 3 and 10 μg/min) and $N^G$-monomethyl-L-arginine (L-NMMA 4 μmol/l). These tests were performed after discontinuation of agents that might have changed vascular function such as ACE inhibitors and calcium channel blockers. Pretreatment with acetylsalicylic acid (aspirin) (650 mg daily taken orally) was given for one week to block prostacyclin and thromboxane generation.

Plethysmography studies were performed during a 5 minute infusion of each agent, diluted in saline and infused at a rate of 1 mL/min into the brachial artery of the non-dominant arm via a thin plastic cannula Each infusion of vasoactive agents was preceded by a period of saline infusion. Bilateral forearm blood flow was measured simultaneously at 15 second intervals for the final two minutes of each 5 minute infusion period employing mercury-in-silastic strain gauges. During measurements hands were excluded from the circulation by inflation of wrist cuffs to 200 mmHg and venous occlusion was obtained by cyclical inflation of upper arm cuffs to 40 mmHg. Results were expressed as the area under the curve (AUC) of the percent increase in forearm blood flow ratio (infused arm versus control arm) to account for any systemic effect of these vasoactive drugs. The AUC provided integration over time of the dose response to the agent used. AUC for percent change in blood flow to ACh was a priori described as the primary efficacy criterion in this trial.

Statistical analyses were performed using 2 by 2 analysis of variance using SPSS package Results:

Out of the 80 patients randomised, 77 completed the 12 week treatment period and paired blood flow data were available in 67; Three withdrawals occurred because of incidental medical conditions and one allergy to fenofibrate. 10 patients refused a second cannulation or could not be cannulated satisfactorily. The four groups were well matched in terms of baseline characteristics as shown on Table 1. Only 8 patients were on oral hypoglycaemic agents, none were on insulin. They presented with good diabetic control and with the typical characteristics of diabetic dyslipidemia.

TABLE 1

Patient characteristics: mean or distribution

|  | PP group | PQ group | PF group | FQ group |
|---|---|---|---|---|
| Gender (M/F) | 14 M/5 F | 18 M/2 F | 14 M/5 F | 14 M/5 F |
| Age (years) | 55 | 53 | 54 | 52 |
| BMI (kg/m$^2$) | 31.0 | 29.9 | 30.0 | 30.6 |
| BP (mm Hg) | 137/78 | 128/76 | 131/74 | 132/77 |
| HbA1c (%) | 6.3 | 6.9 | 7.1 | 7.5 |
| TC (mmol/l) | 5.36 | 5.29 | 5.54 | 5.25 |
| TG (mmol/l) | 2.44 | 2.19 | 2.61 | 2.98 |
| HDL-C (mmol/l) | 1.02 | 0.95 | 0.95 | 0.93 |

Key: P = Placebo; F = Fenofibrate; Q = CoQ$_{10}$
BMI = body mass index; HbA1c = glycosylated hemoglobin A1c
TC = total cholesterol; TG = Triglyceride;
HDL-C = high density lipoprotein cholesterol Table 2 shows the main study results where changes in treatment are presented in a 2×2 table consistent with the factorial study design.

TABLE 2 mean changes and their 95% confidence interval on treatment (Week 12-Week 0) in acetylcholine AUC percent increase in forearm blood flow ratio

|  | P | Q | F− v F+ [95% CI] |
|---|---|---|---|
| P | −23% [−143% to 95%] | −7% [−119% to 105%] | −15% [−97% to 66%] |
| F | 131% [8% to 253%] | 419% [287% to 550%] | 275% [185% to 365%] |
| Q− v Q+ | 53% [−31% to 138%] | 206% [119% to 192%] |  |

Key: P = Placebo; F = Fenofibrate; Q = CoQ$_{10}$
Analysis of variance Interaction p = 0.029, F effect p = 0.0001, Q effect p = 0.015

Figure 1:
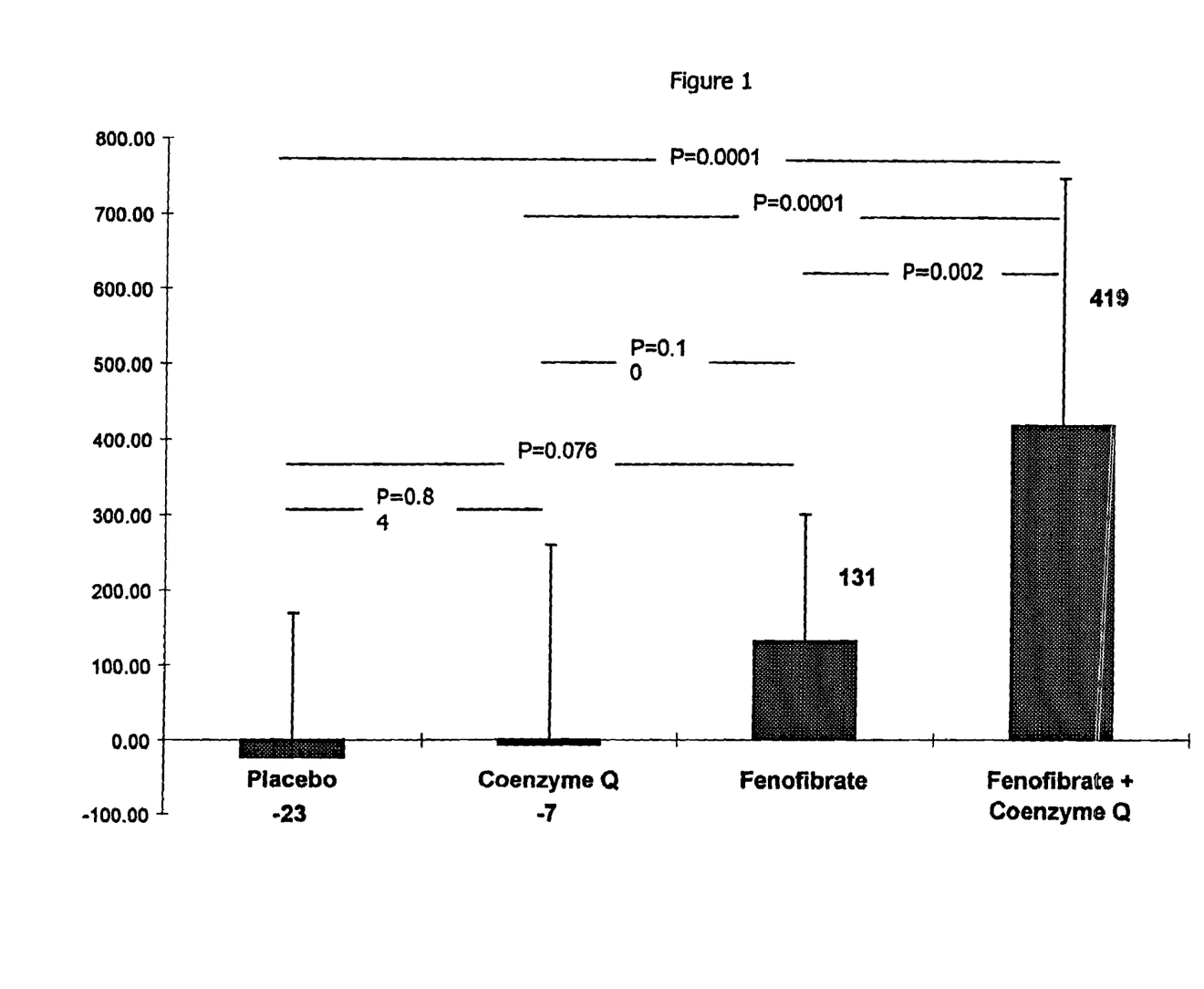
FIG. 1 is a graph showing the acetylcholine percent change in forearm blood flow ratio as a result of the administration of coenzyme $Q_{10}$ and/or fenofibrate.

The combined effect of fenofibrate and CoQ$_{10}$ treatment led to a 419% increase in forearm blood flow ratio, fenofibrate alone to a 131% increase while there was no change with CoQ$_{10}$ alone or placebo. Thus, there was a clear synergism between fenofibrate and CoQ$_{10}$ as evidenced by a significant interaction effect (p=0.029). Changes versus baseline were significant for the fenofibrate alone and the fenofibrate +CoQ$_{10}$ groups but when the 4 groups were compared with each other only the combination treatment was significantly different from the 3 other groups (see FIG. 1)

When the vasodilatory response to ACh was reduced by co-infusion of L-NMMA similar results with a synergism between fenofibrate and coenzyme Q$_{10}$ were observed (see Table 3).

TABLE 3 mean changes and their 95% confidence interval on treatment (Week 12-Week 0) in acetylcholine percent increase in forearm blood flow ratio with co-infusion of L-NMMA

|  | P | Q | F− v F+ [95% CI] |
|---|---|---|---|
| P | 58%[−2% to 118%] | −21% [−76% to 33%] | 18% [−22% to 59%] |
| F | 47%[−10% to 47%] | 118% [53% to 183%] | 83% [39% to 126%] |
| Q− v Q+ | 53% [11% to 94%] | 48% [6% to 90%] |  |

Key: P = Placebo; F = Fenofibrate; Q = CoQ$_{10}$
Analysis of variance Interaction p = 0.015, F effect p = 0.034, Q effect p = 0.884

TABLE 4

Figure 2:
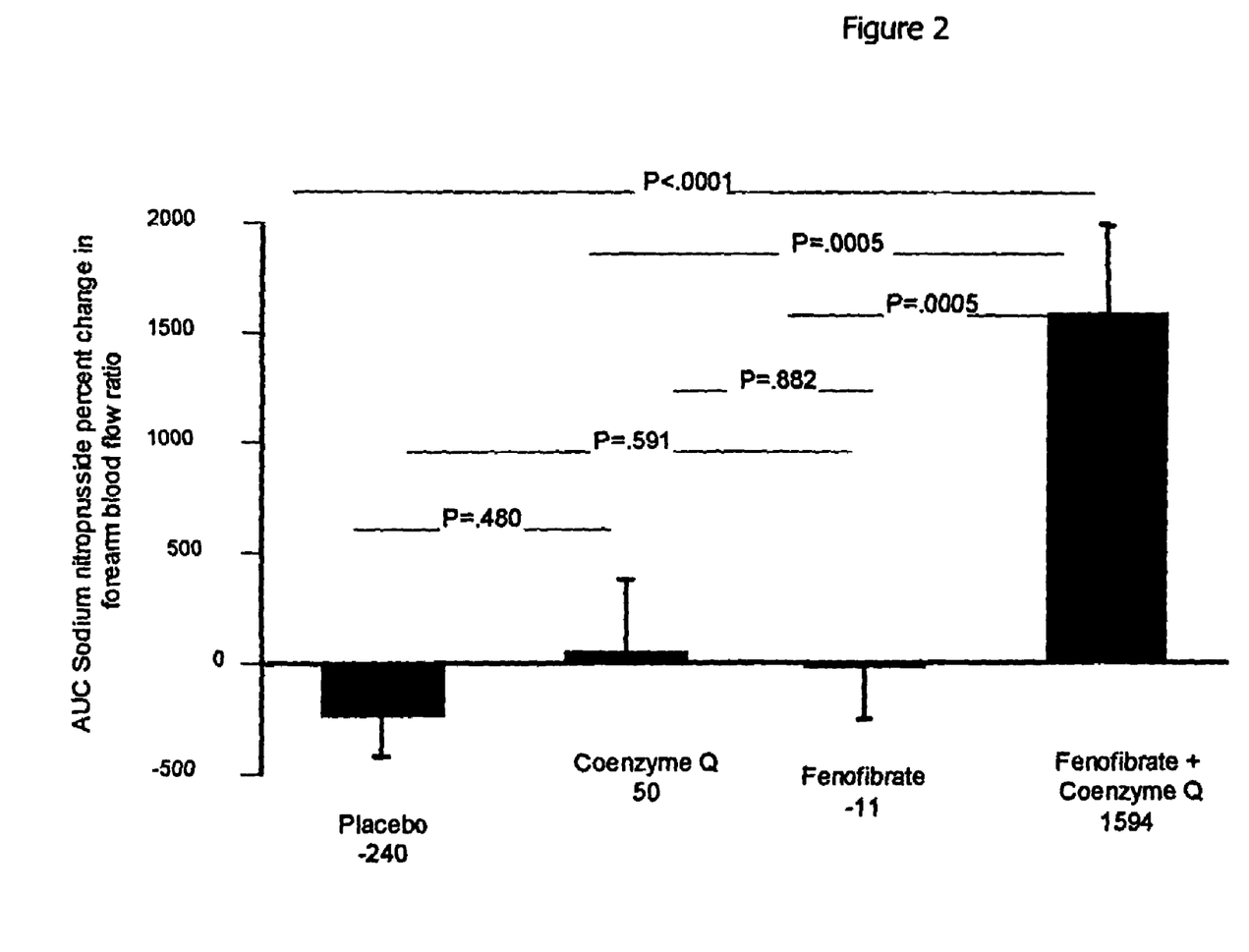
FIG. 2 is a graph showing the sodium nitroprusside percent change in forearm blood flow ratio as a result of the administration of coenzyme $Q_{10}$ and/or fenofibrate.

Mean changes and their 95% confidence interval on treatment (Week 12-week 0) in sodium nitroprusside AUC percent increase in forearm blood flow ratio (see Figure 2)

|  | P | Q | F− v F+ [95% CI] |
|---|---|---|---|
| P | −240%[−632% to 152%] | 50% [−641% to 740%] | −95%[−503% to 313%] |
| F | −11%[−521% to 500%] | 1594%[728% to 2461%] | 792% [352% to 1232%] |
| Q− v Q+ | −126% [−841% to 361%] | 822% [399% to 1245%] |  |

Key: P = Placebo; F = Fenofibrate; Q = CoQ$_{10}$
Analysis of variance Interaction p = 0.032, F effect p = 0.004, Q effect p = 0.002

These improvements in vascular endothelium function were not explained by any interaction between fenofibrate and CoQ$_{10}$ on the lipid modifying properties of fenofibrate; an increase in HDL-cholesterol, a decrease in total cholesterol, LDL-cholesterol, triglyceride or fibrinogen. Furthermore plasma levels of CoQ$_{10}$ after treatment did not differ between the CoQ$_{10}$ alone and the combination groups. There was no change in diabetes control or blood pressure measurements with the combination of fenofibrate and CoQ$_{10}$. CoQ$_{10}$ alone had no lipid lowering effects.

All publications mentioned in the above specification are herein incorporated by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the invention.

REFERENCES

ANDERSON T J, UEHATA A, GERHARD M D, et al. Close relationship of endothelial function in the human coronary and peripheral circulation. J Am Coll Cardiol 1995;26: 1235-41.

COHEN R A. Dysfunction of vascular endothelium in diabetes mellitus. Circulation 1993;97(Suppl V):V67-V76.

ISSEMANN I, GREEN S. Activation of a member of the steroid hormone receptor superfamily by peroxisome proliferators. Nature 1990;347:645-50.

FURCHGOTT R F, ZAWADZKI J V. The obligatory role of endothelial cells in the relaxation of arterial smooth muscle by acetylcholine. Nature 1980: 299:373-376.

GARG U C, HASSID A. Nitric oxide-generating vasodilators and 8-bromocyclic guanosine monophosphate inhibit mitogenesis and proliferation of cultured rat vascular smooth muscle cells. J Clin Invest 1989: 83:1774-1777.

KELLER H., DREYER C., MEDIN J., MAHFOUDI A., OZATO K., WAHLI W. Fatty acids and retinoids control lipid metabolism through activation of peroxisome proliferator-activated receptor-retinoid X receptor heterodimers. Proc. Natl. Acad. Sci. 1993; USA 90:2160-64.

MONCADA S, PALMER R M, HIGGS E A. Nitric oxide: physiology, pathophysiology, and pharmacology. Pharmacol. Rev 1991: 43:109-142.

RADOMSKI M W, PALMER R M, MONCADA S. Endogenous nitric oxide inhibits human platelet adhesion to vascular endothelium. Lancet 1987: 2:1057:1058.

RUBANYI G M. The role of endothelium in cardiovascular homeostasis and diseases. J Cardiol Pharmacol 1993;22 (suppl 4):51-514.

SAX F L, CANNON R O III, HANSON C, EPSTEIN S E. Impaired forearm vasodilator reseve in patients with microvascular angina. Evidence of a generalized disorder of vascular function? N Engl J Med 1987;317:1366-70.

SCHACHINGER V, BRITTEN M B, ZEIHER A M. Prognostic impact of coronary vasodilator dysfunction on adverse long-term outcome of coronary heart disease. Circulation 2000;101:1899-1906.

SUWAIDI J S, HAMASAKI S, HIGANO S T, et al. Long term follow-up of patients with mild coronary artery disease and endothelial dysfunction. Circulation 2000;101:948-54.

WATTS G F, PLAYFORD D A. Dyslipoproteinemia and hyperoxidative stress in the pathogenesis of endothelial dysfunction in non-insulin dependent diabetes mellitus: an hypothesis Atherosclerosis 1998;141:17-30.

The invention claimed is:

1. A method for treating a disorder characterized by endothelial dysfunction in a mammal, the method comprising:
    administering daily to the mammal a composition comprising:
        about 200 mg of fenofibrate or a pharmaceutically acceptable salt thereof; and
        about 200 mg of coenzyme $Q_{10}$ or a pharmaceutically acceptable salt thereof;
    the disorder being cardiovascular disease, hypertension, stroke, myocardial infarction, peripheral vascular disease, macro angiopathy in the mammal with diabetes, or micro angiopathy in the mammal with diabetes.

2. The method of claim 1, comprising administering daily to the mammal a composition comprising:
    200 mg of fenofibrate or a pharmaceutically acceptable salt thereof; and
    200 mg of coenzyme $Q_{10}$ or a pharmaceutically acceptable salt thereof.

* * * * *